(12) United States Patent
Brugger et al.

(10) Patent No.: US 9,533,088 B2
(45) Date of Patent: Jan. 3, 2017

(54) METHODS AND APPARATUS FOR LEAK DETECTION IN BLOOD PROCESSING SYSTEMS

(71) Applicant: NXSTAGE MEDICAL, INC., Lawrence, MA (US)

(72) Inventors: James M. Brugger, Newburyport, MA (US); Christopher McDowell, Holladay, UT (US)

(73) Assignee: NXSTAGE MEDICAL, INC., Lawrence, MA (US)

( * ) Notice: Subject to any disclaimer, the term of this patent is extended or adjusted under 35 U.S.C. 154(b) by 263 days.

(21) Appl. No.: 13/928,622

(22) Filed: Jun. 27, 2013

(65) Prior Publication Data

US 2013/0283891 A1    Oct. 31, 2013

Related U.S. Application Data

(60) Continuation of application No. 13/075,454, filed on Mar. 30, 2011, now Pat. No. 8,480,608, which is a
(Continued)

(51) Int. Cl.
*A61M 37/00* (2006.01)
*A61M 1/36* (2006.01)
*A61M 39/22* (2006.01)

(52) U.S. Cl.
CPC .......... *A61M 1/367* (2013.01); *A61M 1/3626* (2013.01); *A61M 1/3653* (2013.01);
(Continued)

(58) Field of Classification Search
CPC A61M 1/3656; A61M 1/3626; A61M 39/223; A61M 2205/15
(Continued)

(56) References Cited

U.S. PATENT DOCUMENTS 3,744,524 A  7/1973 Blau
3,985,134 A  10/1976 Lissot et al.
(Continued)

FOREIGN PATENT DOCUMENTS

JP  03-223576  10/1991
JP  07-248066  9/1995
(Continued)

OTHER PUBLICATIONS

International Preliminary Report on Patentability dated Mar. 7, 2007 in International Application No. PCT/US04/36933.
(Continued)

*Primary Examiner* — Leslie Deak
(74) *Attorney, Agent, or Firm* — Potomac Law Group, PLLC; Mark Catan

(57) ABSTRACT

A flow reversing device for performing blood treatment can include a flow reversing actuator. The flow reversing actuator can receive and engage a disposable tubing set with multiple branches that form forward and reverse blood flow paths respectively when blood the flow reversing actuator is selectively changed between forward and reverse configurations. The shape of the tubing can be such that during forward operation, dead regions of non-flowing blood are defined. The flow reversing actuator can have a controller configured to operate generally in forward mode. At first times, the controller can cause the flow reversing actuator to clear the dead regions. At second times, the controller can cause the flow reversing actuator to test for leaks by reversing the flow of blood for a period of time sufficient to cause air to be drawn into the tubing set and conveyed to an air sensor.

15 Claims, 15 Drawing Sheets

Related U.S. Application Data division of application No. 10/578,600, filed as application No. PCT/US2004/036933 on Nov. 5, 2004, now Pat. No. 8,002,727.

(60) Provisional application No. 60/518,122, filed on Nov. 7, 2003.

(52) U.S. Cl.
CPC ........ *A61M 1/3656* (2014.02); *A61M 39/223* (2013.01); *A61M 2205/15* (2013.01); *Y10T 137/86831* (2015.04)

(58) Field of Classification Search
USPC ............... 604/4.01, 5.01, 6.01, 6.1, 6.16, 27–32,604/167.05, 248; 210/645, 646; 137/625.14, 137/625, 625.11, 625.42, 625.43
See application file for complete search history.

(56) References Cited

U.S. PATENT DOCUMENTS

| | | | |
|---|---|---|---|
| 4,160,727 A | 7/1979 | Harris, Jr. | |
| 4,468,329 A | 8/1984 | Shaldon et al. | |
| 4,495,067 A | 1/1985 | Klein et al. | |
| 4,614,590 A | 9/1986 | Rath et al. | |
| 4,666,598 A | 5/1987 | Heath et al. | |
| 4,770,787 A | 9/1988 | Heath et al. | |
| 4,784,763 A | 11/1988 | Hambleton et al. | |
| 4,885,087 A | 12/1989 | Kopf | |
| 5,004,535 A | 4/1991 | Bosko et al. | |
| 5,032,265 A | 7/1991 | Jha et al. | |
| 5,120,303 A | 6/1992 | Hombrouckx | |
| 5,259,954 A | 11/1993 | Taylor | |
| 5,312,547 A | 5/1994 | Kruger et al. | |
| 5,352,364 A | 10/1994 | Kruger et al. | |
| 5,498,338 A | 3/1996 | Kruger et al. | |
| 5,605,630 A | 2/1997 | Shibata | |
| 5,687,764 A | 11/1997 | Tanaka et al. | |
| 5,690,829 A | 11/1997 | Lauer | |
| 5,830,365 A | 11/1998 | Schneditz | |
| 5,894,011 A | 4/1999 | Prosl et al. | |
| 5,951,863 A | 9/1999 | Kruger et al. | |
| 5,951,870 A | 9/1999 | Utterberg | |
| 6,044,691 A | 4/2000 | Kenley et al. | |
| 6,048,727 A | 4/2000 | Kopf | |
| 6,090,048 A | 7/2000 | Hertz et al. | |
| 6,177,049 B1 | 1/2001 | Schnell et al. | |
| 6,189,388 B1 | 2/2001 | Cole et al. | |
| 6,221,040 B1 | 4/2001 | Kleinekofort | |
| 6,308,737 B1 * | 10/2001 | Krivitski ................ 137/597 |
| 6,319,465 B1 | 11/2001 | Schnell et al. | |
| 6,572,576 B2 | 6/2003 | Brugger et al. | |
| 6,582,385 B2 | 6/2003 | Burbank et al. | |
| 6,596,234 B1 | 7/2003 | Schnell et al. | |
| 6,649,003 B1 | 11/2003 | Spain et al. | |
| 6,679,988 B2 | 1/2004 | Gsell | |
| 6,695,807 B2 | 2/2004 | Bell et al. | |
| 6,745,903 B2 | 6/2004 | Grandics | |
| 6,855,121 B1 | 2/2005 | Chan et al. | |
| 6,881,337 B2 | 4/2005 | Meluch et al. | |
| 6,929,743 B2 | 8/2005 | Diel | |
| 7,040,142 B2 | 5/2006 | Burbank | |
| 7,674,237 B2 | 3/2010 | O'Mahony et al. | |
| 8,002,727 B2 * | 8/2011 | Brugger et al. ............ 604/6.1 |
| 8,480,608 B2 * | 7/2013 | Brugger et al. ............ 604/6.01 |
| 2002/0017489 A1 | 2/2002 | Utterberg | |
| 2003/0009123 A1 * | 1/2003 | Brugger et al. ............ 604/4.01 |
| 2004/0026315 A1 | 2/2004 | Han et al. | |
| 2004/0186415 A1 | 9/2004 | Burbank et al. | |
| 2008/0214979 A1 | 9/2008 | Brugger et al. | |
| 2010/0021315 A1 | 1/2010 | Wolff | |

FOREIGN PATENT DOCUMENTS

| | | |
|---|---|---|
| WO | WO 03/006944 | 1/2003 |
| WO | WO 04/001438 | 12/2003 |

OTHER PUBLICATIONS

International Search Report and Written Opinion dated Nov. 14, 2005 in International Application No. PCT/US04/36933.
Office Action dated May 26, 2009 in Japanese Application No. 2006-538506.
Supplementary European Search Report dated Jul. 30, 2009 in European Application No. 04810398.
U.S. Appl. No. 10/037,429, filed Jul. 10, 2003.
U.S. Appl. No. 10/393,209, filed Sep. 23, 2004.

* cited by examiner

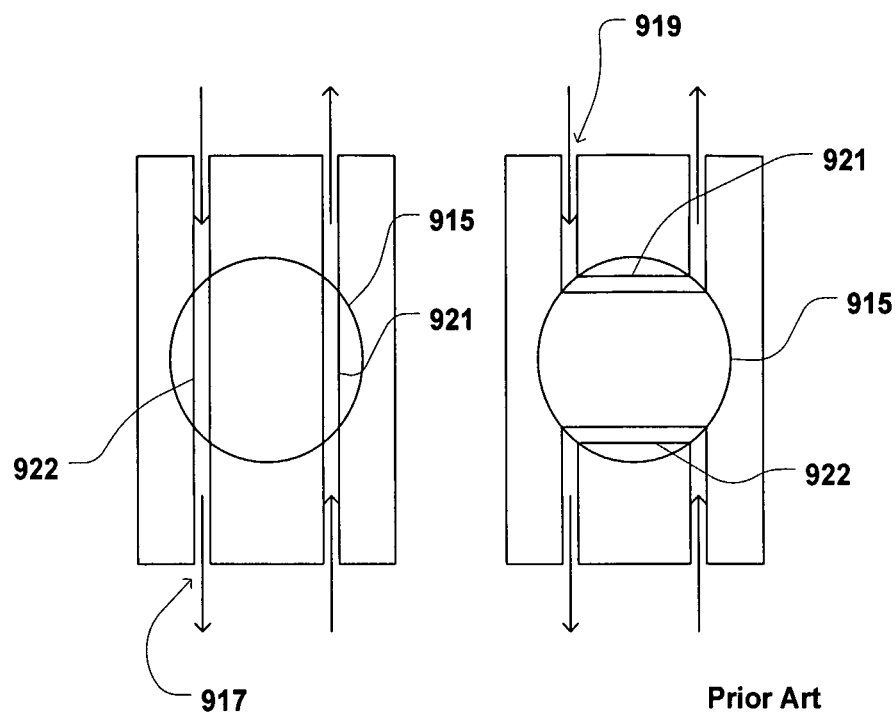
Fig. 1C
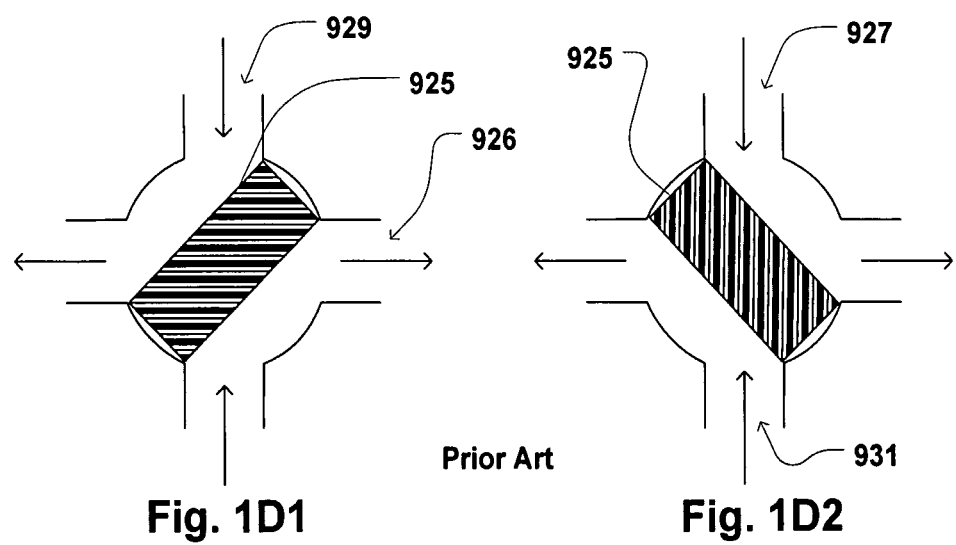
Fig. 1D1    Fig. 1D2

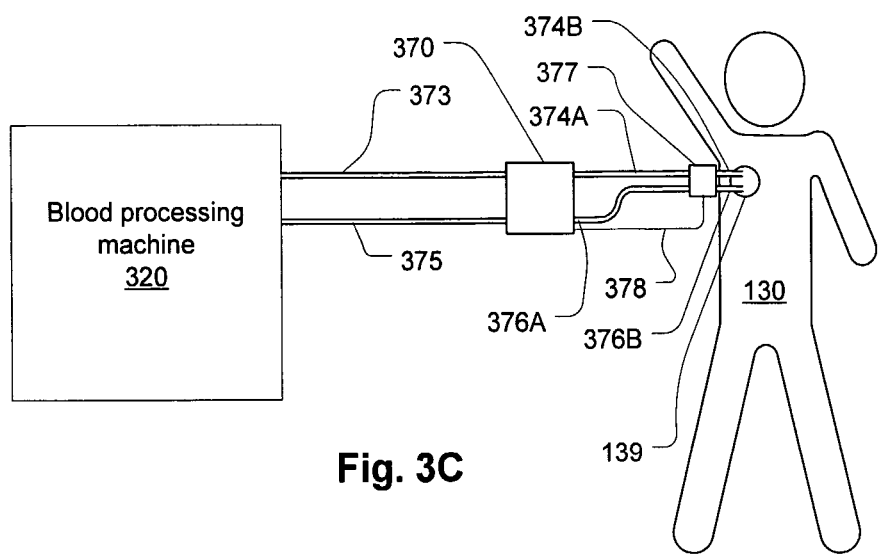
Fig. 3C
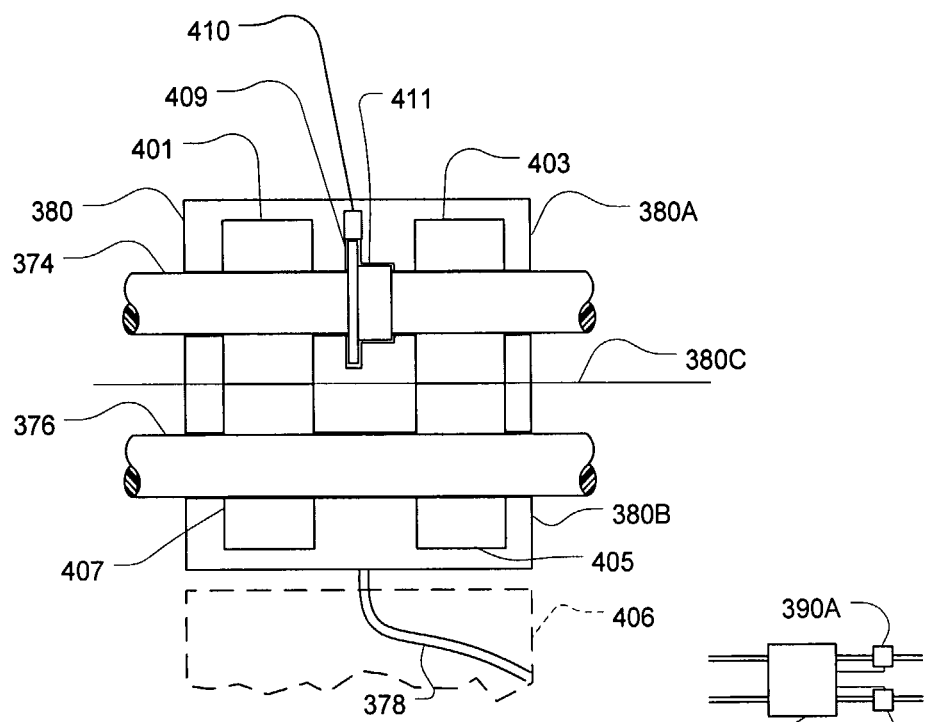
Fig. 3D
Fig. 3E

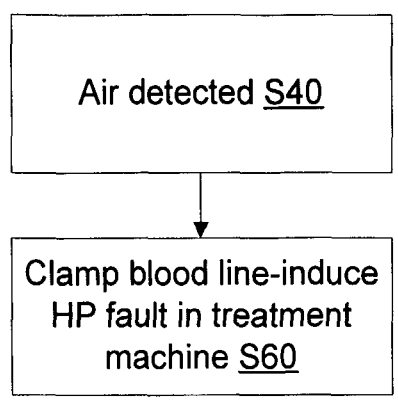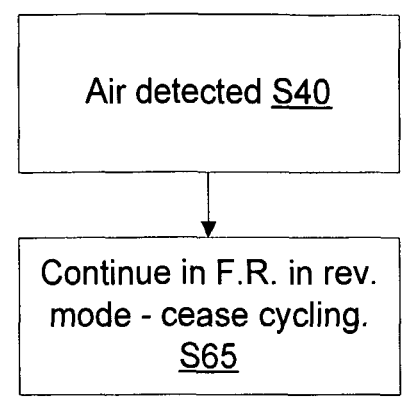
S45A
S45B
Fig. 14A
Fig. 14B

METHODS AND APPARATUS FOR LEAK DETECTION IN BLOOD PROCESSING SYSTEMS

CROSS-REFERENCE TO RELATED APPLICATIONS

The present application is a continuation of U.S. application Ser. No. 13/075,454, filed Mar. 30, 2011, which is a division of U.S. application Ser. No. 10/578,600, filed May 8, 2006 (§371(c) date of Mar. 31, 2008), now U.S. Pat. No. 8,002,727, which is a U.S. national stage entry of International Application No. PCT/US2004/036933, filed Nov. 5, 2004, which claims the benefit of U.S. Provisional Application No. 60/518,122, filed Nov. 7, 2003.

FIELD

The present invention relates to the detection of leaks (including needle-disconnects and other causes of loss of integrity) in extracorporeal blood circuits and more particularly to the application of air infiltration detection techniques to the detection of leaks in positive pressure return lines.

BACKGROUND

Many medical procedures involve the extraction and replacement of flowing blood from, and back into, a donor or patient. The reasons for doing this vary, but generally, they involve subjecting the blood to some process that cannot be carried out inside the body. When the blood is outside the patient it is conducted through machinery that processes the blood. The various processes include, but are not limited to, hemodialysis, hemofiltration, hemodiafiltration, blood and blood component collection, plasmaphresis, aphresis, and blood oxygenation.

One technique for extracorporeal blood processing employs a single "access," for example a single needle in the vein of the patient or a fistula. A volume of blood is cyclically drawn through the access at one time, processed, and then returned through the same access at another time. Single access systems are uncommon because they limit the rate of processing to half the capacity permitted by the access. As a result, two-access systems, in which blood is drawn from a first access, called an arterial access, and returned through a second access, called a venous access, are much faster and more common. These accesses include catheters, catheters with subcutaneous ports, fistulas, and grafts.

The processes listed above, and others, often involve the movement of large amounts of blood at a very high rate. For example, 500 ml of blood may be drawn out and replaced every minute, which is about 5% of the patient's entire supply. If a leak occurs in such a system, the patient could be drained of enough blood in a few minutes to cause loss of consciousness with death following soon thereafter. As a result, such extracorporeal blood circuits are normally used in very safe environments, such as hospitals and treatment centers, and attended by highly trained technicians and doctors nearby. Even with close supervision, a number of deaths occur in the United States every year due to undue blood loss from leaks.

Leaks present a very real risk. Leaks can occur for various reasons, among them: extraction of a needle, disconnection of a luer, poor manufacture of components, cuts in tubing, and leaks in a catheter. However, in terms of current technology, the most reliable solution to this risk, that of direct and constant trained supervision in a safe environment, has an enormous negative impact on the lifestyles of patients who require frequent treatment and on labor requirements of the institutions performing such therapies. Thus, there is a perennial need in the art for ultra-safe systems that can be used in a non-clinical setting and/or without the need for highly trained and expensive staff. Currently, there is great interest in ways of providing systems for patients to use at home. One of the risks for such systems is the danger of leaks. As a result, a number of companies have dedicated resources to the solution of the problem of leak detection.

In single-access systems, loss of blood through the patient access and blood circuit can be indirectly detected by detecting the infiltration of air during the draw cycle. Air is typically detected using an ultrasonic air detector on the tubing line, which detects air bubbles in the blood. The detection of air bubbles triggers the system to halt the pump and clamp the line to prevent air bubbles from being injected into the patient. Examples of such systems are described in U.S. Pat. Nos. 3,985,134, 4,614,590, and 5,120,303.

While detection of air infiltration is a reliable technique for detecting leaks in single access systems, the more attractive two-access systems, in which blood is drawn continuously from one access and returned continuously through another, present problems. While a disconnection or leak in the draw line can be sensed by detecting air infiltration, just as with the single needle system, a leak in the return line cannot be so detected. This problem has been addressed in a number of different ways, some of which are generally accepted in the industry.

The first level of protection against return line blood loss is the use of locking luers on all connections, as described in International Standard ISO 594-2 which help to minimize the possibility of spontaneous disconnection during treatment. Care in the connection and taping of lines to the patient's bodies is also a known strategy for minimizing this risk.

A higher level of protection is the provision of venous pressure monitoring, which detects a precipitous decrease in the venous line pressure. This technique is outlined in International Standard IEC 60601-2-16. This approach, although providing some additional protection, is not very robust, because most of the pressure loss in the venous line is in the needle used to access the patient. There is very little pressure change in the venous return line that can be detected in the event of a disconnection, so long as the needle remains attached to the return line. Thus, the pressure signal is very weak. The signal is no stronger for small leaks in the return line, where the pressure changes are too small to be detected with any reliability. One way to compensate for the low pressure signal is to make the system more sensitive, as described in U.S. Pat. No. 6,221,040, but this strategy can cause many false positives. It is inevitable that the sensitivity of the system will have to be traded against the burden of monitoring false alarms. Inevitably this leads to compromises in safety. In addition, pressure sensing methods cannot be used at all for detecting small leaks.

Yet another approach, described for example in PCT application US98/19266, is to place fluid detectors near the patient's access and/or on the floor under the patient. The system responds only after blood has leaked and collected in the vicinity of a fluid detector. A misplaced detector can defeat such a system and the path of a leak cannot be reliably predicted. For instance, a rivulet of blood may adhere to the patient's body and transfer blood to points remote from the detector. Even efforts to avoid this situation can be defeated by movement of the patient, deliberate or inadvertent (e.g., the unconscious movement of a sleeping patient).

Still another device for detecting leaks is described in U.S. Pat. No. 6,044,691. According to the description, the circuit is checked for leaks prior to the treatment operation. For example, a heated fluid may be run through the circuit and its leakage detected by means of a thermistor. The weakness of this approach is immediately apparent: there is no assurance that the system's integrity will persist, throughout the treatment cycle, as confirmed by the pre-treatment test. Thus, this method also fails to address the entire risk.

Yet another device for checking for leaks in return lines is described in U.S. Pat. No. 6,090,048. In the disclosed system, a pressure signal is sensed at the access and used to infer its integrity. The pressure wave may be the patient's pulse or it may be artificially generated by the pump. This approach cannot detect small leaks and is not very sensitive unless powerful pressure waves are used, in which case the effect can produce considerable discomfort in the patient.

Clearly detection of leaks by prior art methods fails to reduce the risk of dangerous blood loss to an acceptable level. In general, the risk of leakage-related deaths increases with the decrease in medical staff per patient driven by the high cost of trained staff. Currently, with lower staffing levels comes the increased risk of unattended leaks. Thus, there has been, and continues to be, a need in the prior art for a foolproof approach to detection of a return line leak or disconnection.

In an area unrelated to leak detection, U.S. Pat. No. 6,177,049 B1 suggests the idea of reversing the direction of blood flow for purposes of patency testing. The patent also states that flow reversal may be used to improve patency by clearing obstructed flow.

U.S. Pat. No. 6,572,576 discusses various embodiments of a blood treatment device where blood flow is reversed to provide leak detection. According to the inventions described, a leak detector effective to ensure detection of leaks in the venous blood line (the line returning blood to the patient) is provided by periodically generating a negative pressure, which may be brief or at a 50% duty cycle, in the blood return line. This draws air into the venous line which can be revealed by an air sensor in the blood treatment machine. During the negative pressure cycle, any air drawn in the venous blood line is detected, the system is shut down and an alarm generated. U.S. Pat. No. 6,572,576, filed Jul. 7, 2001 entitled "Method and apparatus for leak detection in a fluid line" is hereby incorporated by reference as if fully set forth in its entirety herein.

Hemofiltration, dialysis, hemodiafiltration, and other extracorporeal blood treatments may employ flow selector valves such as Y-valves, four-way valves, and other such devices for redirecting the flow of blood and other fluids such as replacement fluids. For example, the direction of the flow of blood through certain types of filters may be reversed repeatedly to prevent coagulation of blood in regions where the mean flow slows to very low rates. For example, where blood is circulated through tubular media in the context of a dialysis filter, it has been proposed that blood may coagulate on the surface of the inlet header leading to the progressive coagulation of blood. U.S. Pat. No. 5,605,630 proposes occasionally reversing the flow of blood through the filter. A four-way valve is proposed for changing over the flow direction.

In other references, the idea of reversing the flow of blood through a tubular media filter is discussed in connection with other issues. For example, in U.S. Pat. No. 5,894,011, the known technique of switching access lines in the patient to improve the flow through an occluded fistula is automated by the addition of a four-way valve on the patient-side blood circuit. In single-access systems in general, for example as described in U.S. Pat. No. 5,120,303, flow is conventionally reversed through the filter during each draw/return cycle. In the '303 reference, the specification observes that the efficiency of filtration is increased due to the double-passing of the same blood through the filter; that is, each volume of drawn blood is filtered twice. Yet another reference, U.S. Pat. No. 6,189,388 B1, discusses reversing the flow direction of blood through the patient access occasionally in order to quantify an undesirable short-circuit effect that attends their long term use. Still another U.S. Pat. No. 6,177,049 B1 suggests reversing flow through the draw access before treatment while an observer is present to test the accesses for patency or to clear blockage in the accesses.

Referring to FIGS. 1A through 1E, a number of alternative designs for four-way valves have been developed for blood circuits. Referring to FIG. 1A, U.S. Pat. No. 5,894,011, discloses a valve that swaps the connections between pairs of lines 905 and 906 via a pair of rotatably connected disks 901 and 902, each of which supports one of the pairs of lines 905 and 906. A seal must be maintained between the disks 901 and 902 and between the respective lines. The device is intended to be operated manually.

Referring to FIG. 1B, another four-way valve, disclosed in U.S. Pat. No. 5,605,630, which has been proposed for use in blood lines, has a rotating wheel 910 with channels 911 and 912 defined between the wheel 910 and the inside of a housing 913. When the wheel is rotated, the channels 911 and 912 shift to join a different pair of lines. This device also has seals.

Referring to FIG. 1C, another arrangement is proposed in U.S. Pat. No. 6,177,049. This device has a rotating component 915 with channels 921 and 922 defined within it. As the rotating component 915 is rotated, the channels defined between pairs of lines 917 and 919 change from parallel lines joining one set of corresponding lines to U-shaped channels joining a different set.

Referring to FIGS. 1D1 and 1D2, a design, disclosed in U.S. Pat. No. 4,885,087, is very similar to that of FIG. 1B. This design has a rotator 925 that connects different pairs of lines depending on the position thereby defining two different sets of possible flow channels 926 and 929 or 927 and 931.

In all of the above designs, the valves are not hermetically sealed. Any seal can be compromised, particularly by microorganisms. Thus, each of the foregoing designs suffers from that drawback. Also, many are expensive and do not lend themselves to automation.

Referring to FIG. 1E, another type of four-way valve is formed by interconnecting two tubes 937 and 938 with crossover lines 935 and 936. This design is disclosed in U.S. Pat. No. 6,189,388 (Hereafter, "U.S. Pat. No. '388"). Tube pinching actuators 941-944 are used to force fluid through different channels, depending on which actuators are closed. This device provides a hermetic seal and can be fairly inexpensive, but in a given configuration, significant no-flow areas are defined. These dead spaces can lead to the coagulation of blood, which is undesirable. Also, the interconnection of tubes in this does not lend itself to automated manufacturing.

BRIEF DESCRIPTION OF THE DRAWINGS

FIGS. 1A, 1B, 1C, 1D1, 1D2, and 1E illustrate various flow reversing devices according to the prior art.

FIG. 3C illustrates a flow circuit including a blood treatment machine, a flow reversing module, and a sensor module.

FIG. 3D illustrates details of a sensor module.

FIG. 3E illustrates a detail of a flow circuit with a flow reversing module and separate sensor modules.

FIGS. 14A and 14B illustrate control responses to air detection, according to an embodiment of the invention.

DETAILED DESCRIPTION

Figure 1A:
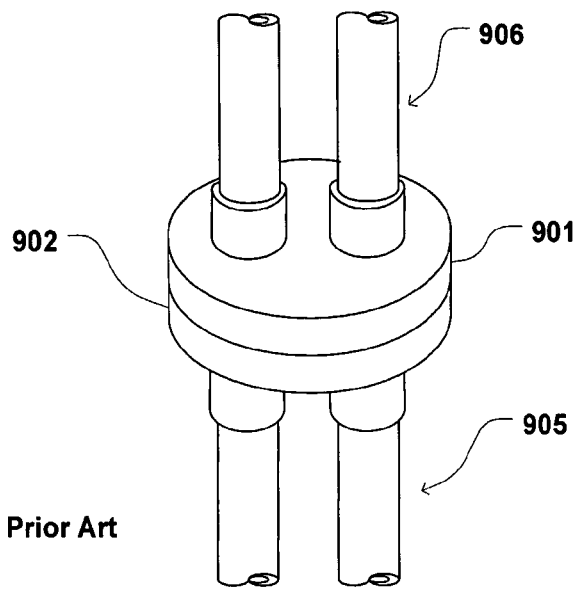
Figure 1B:
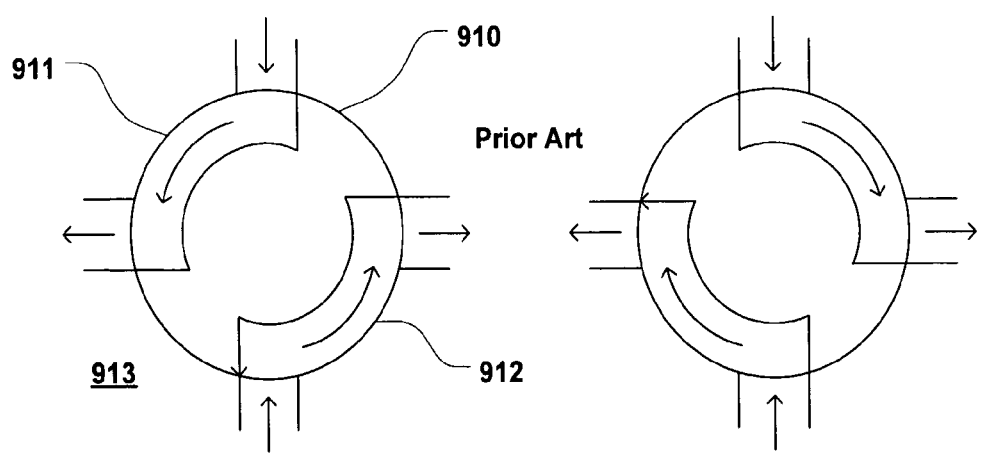
Figure 1E:
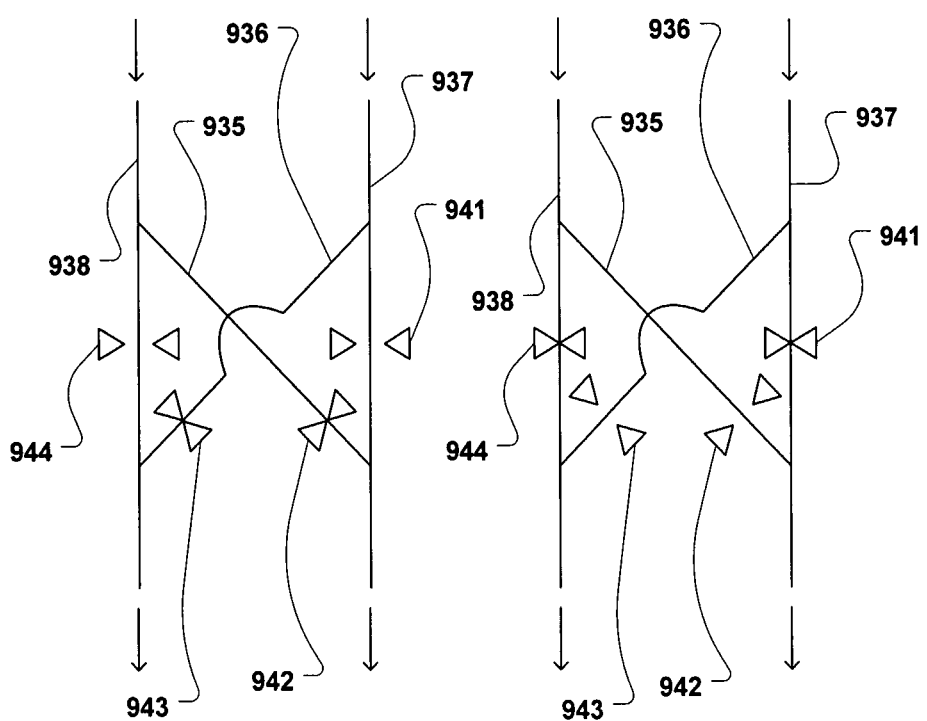
Figure 2A:
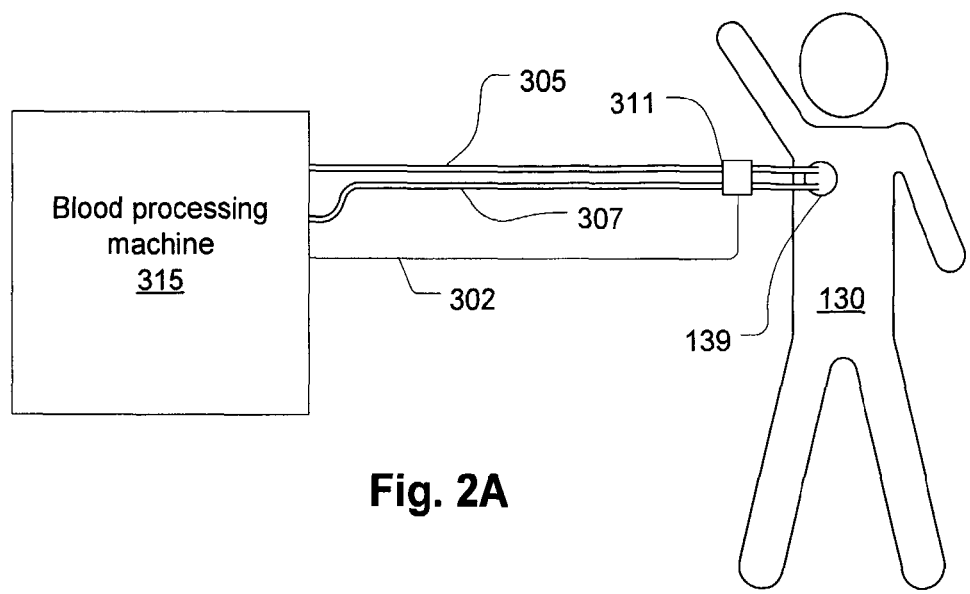
FIG. 2A illustrates a flow circuit including a blood treatment machine and a sensor module.

Referring now to FIG. 2A, a patient 130 is connected by an access 139 to a blood processing machine 315. The latter draws blood through an arterial blood line 305 and returns treated blood to the patient 130 through a venous blood line 307. The blood processing machine 315 may be any treatment device such as a hemodialysis machine, a hemofiltration machine, an infusion pump (in which case no arterial line 305 would be present), etc.

Access 139 may consist of various devices such as a fistula (not shown) and catheter (not shown) combination or other type of access which may be disconnected by various means. For example, a catheter (not shown) may be withdrawn from a fistula (not shown) and/or the catheter (not shown) disconnected from the arterial 307 and venous 305 lines by means of a luer connector (not shown). The above are conventional features of which a variety of alternatives are known.

One or more bubble or air sensors (not shown) are provided in a sensor module 311. The sensor module 311 is connected to the blood processing machine 315 by means of a signal line 302. The signal line 302 applies a signal indicating the presence of air or bubbles in one or both of the arterial 307 and venous 305 lines. The sensor module 311 may be lightweight snap-on module that clamps onto the arterial 307 and venous 305 lines. As is common in blood treatment systems, the arterial 307 and venous 305 lines are clear plastic such as PVC. The sensor module 311 may also include a sensor to indicate the presence of blood in the arterial 307 and venous 305 lines as well. The latter signal may be used for indicating and controlling a transition from a priming mode where the arterial 307 and venous 305 lines carry sterile fluid to a treatment mode where the arterial 307 and venous 305 lines carry blood.

Figure 2B:
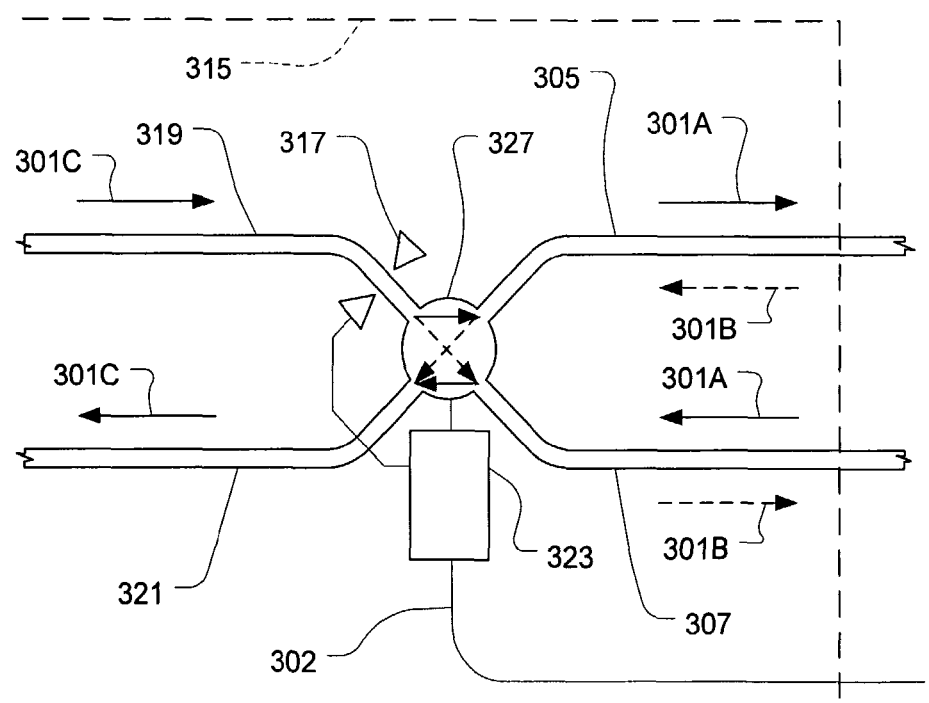
FIG. 2B illustrates a flow reversing portion of the blood treatment machine of FIG. 2A.

Referring now also to FIG. 2B, the blood processing machine 315 may include, along with various other hardware elements, a flow reversing valve 327. The flow reversing valve 327 may be controlled by an electronic controller 323 to cause the flow through the arterial 307 and venous 305 lines to reverse. In a normal treatment mode, the flow may be as indicated by arrows 301A and during a test mode, in which flow is reversed, blood flow may be as indicated by arrows 301B. During both treatment and test modes, the flow of blood on the other side of the reversing valve 327 may remain as indicated by arrows 301C.

During treatment, the reversing valve 327 is periodically actuated to place the reversing valve 327 in the test mode. This generates a negative gage pressure in the venous line 305. If any leaks are present in the venous line 305 between the patient 130 and the sensor module 311, air will infiltrate the venous line 305 and be detected by the air or bubble detector within the sensor module 311. The resulting signal may be applied to the controller 323. The controller 323 may be configured to respond by controlling one or more line clamps as indicated at 317 to stop the flow of blood and trigger an over-pressure alarm in the blood processing machine 315 if the latter is provided with one. The controller may also activate an alarm (not shown). The controller may alternatively maintain the test mode to continue flow in the reversed direction in which case, if the blood processing machine 315 is provided with an internal air or bubble detector (not shown), the latter will be triggered by the infiltrating air as if the air had been drawn by the arterial line in the first instance.

Although a flow reversing valve 327 is illustrated in FIG. 2B, alternative mechanisms for generating a negative pressure in the venous line 305 as discussed in references incorporated by reference in the instant specification. Also, while one line clamp 317 is illustrated, more clamps may be employed to prevent the loss of blood. For example, a clamp may be provided in the venous line 305. Note that the use of a sensor module 311 as illustrated allows the sensors to be located close to the patient. consequently, the system can respond quickly to a disconnection of the arterial 307 or venous 305 lines. One of the common types of leaks the system may protect against is an improperly installed or defective connection between the venous 305 or arterial 307 line and the catheter (not shown).

Figure 3A:
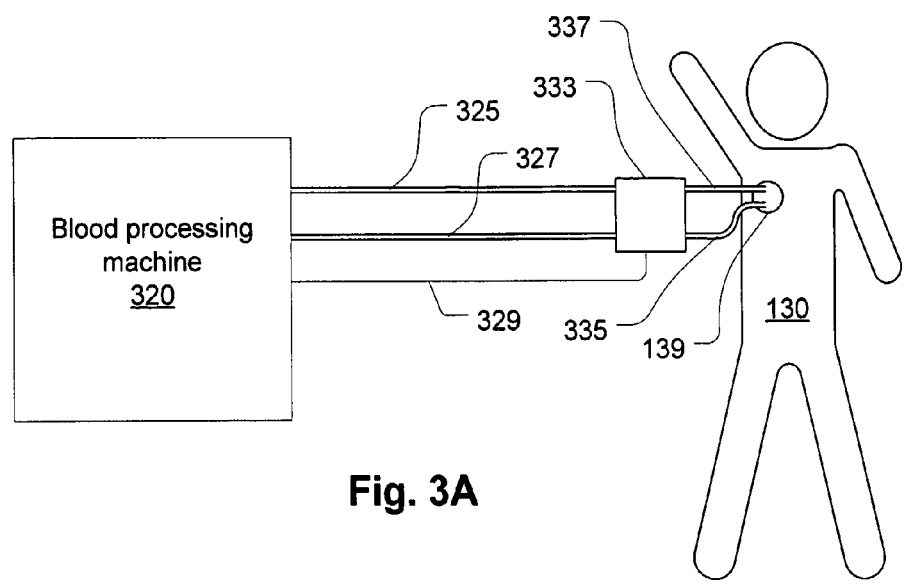
FIG. 3A illustrates a flow circuit including a blood treatment machine, a flow reversing module.
Figure 3B:
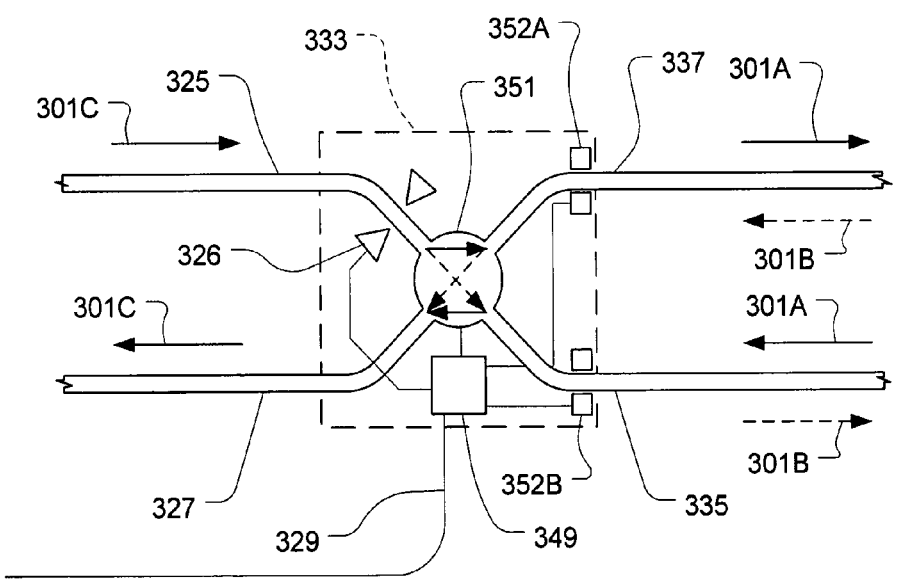
FIG. 3B illustrates features of the flow reversing module of FIG. 3A.

Referring now to FIGS. 3A and 3B, a combined flow reversing and sensor module 333 houses a flow reversing valve 351 and at least one sensor 352A. Flow through venous 325 and arterial 327 lines may be reversed in portions 337 and 335, respectively, by reversing the flow reversing valve 351. The sensor 352A may include a bubble or air sensor, a blood sensor, or both. The sensor module 333 or any of the other sensor modules described herein may include other types of sensors such as pressure sensors to detect a loss of patency at any point in the system. In the foregoing embodiments, the blood or air (or bubble) sensors may include non-wetted conductivity sensors or non-wetted conductivity cells such as optical (opacity or hue) sensors or any sensor suitable for detecting the presence of air or blood in a clear liquid. The sensor module may also be used to detect other properties or conditions near the patient access such as a sudden acceleration (by means of an accelerometer) due to detachment and subsequent falling out of a catheter, for example. An additional sensor 352B, which may be identical to sensor 352A, may be employed to provide an indication of air infiltration during normal operation in a forward blood-flow direction.

A controller 349 may be provided to periodically control the flow reversing valve 351. The controller may activate a line clamp 326. The controller may respond to the detection of air in the same manner as described with respect to the foregoing embodiments or as described in the references incorporated in the instant specification, for example, by clamping the line. A signal line 329 may be provided to transmit detector and/or controller signals to the blood processing machine 320. Blood processing machine 320 may be similar to that described with reference to the previous embodiments (e.g. 315 in FIGS. 2A and 2B), but preferably it does not include the reversing valve 351. As in previous embodiment, in a normal treatment mode, the flow may be as indicated by arrows 301A and during a test mode, in which flow is reversed; blood flow may be as indicated by arrows 301B. During both treatment and test modes, the flow of blood on the other side of the reversing valve 351 may remain as indicated by arrows 301C.

Referring now to FIG. 3C, the blood processing machine 320, the same as the one described with reference to FIG. 3A, is linked by venous 373 and arterial 375 blood lines to a flow reversing module 370. A sensor module 377 is located close to the access 139 and is coupled to the reversing module 370 by a signal line 378. Venous 374A and arterial 376A lines link the reversing module 370 to the access 139 for supply and return flows of blood (with reference to the patient 130), respectively. Portions of venous 374B and arterial 376B lines pass through the sensor module 377 to the access 139. The configuration of FIG. 3C, as in the configuration of FIGS. 2A and 2B allows the sensor module 377 to be located close to the patient 130 and for the reversing module 370 to be retrofitted to a blood treatment machine 315 that is otherwise not configured for leak detection in the fashion described. Thus FIGS. 3A-3C are attractive for retrofit applications where leak detection capability is to be added to a blood processing machine 315 otherwise not configured for it.

Internally, the flow reversing module 370 may be identical to that shown in FIG. 3B. The sensor(s) 352 may or may not be present to protect against leaks in the portions of the venous and arterial lines 374A and 376A as well as the portions 374B and 376B which are protected by sensors in the sensor module 377. Note also that signal line 378 or any of the foregoing signal lines may represent wireless links, acoustical signal links, or any suitable means of communication. Also, the various devices may be powered by battery or by electrical lines.

Referring to FIG. 3D, a sensor module 380 has features which may be employed in sensor modules 311 (FIG. 2A) and 377 (FIG. 3C) described above. Air detectors 401 and 407 detect air passing through lines 374 and 376, respectively. Blood sensors 403 and 405 may be included in the sensor module 380 to detect blood in lines 374 and 376, respectively. Note that in another embodiment, the sensor module 380 only contains sensors for a single line 374, which is preferably the venous line of the foregoing embodiments. In yet another embodiment, the entire sensor module 380 is connected around a single line 374, which is preferably the venous line of the foregoing embodiments. In the latter case, only the upper part 380A is present and the other half 380B on the other side of line 380C is not present. Note that alternatively, both lines may be provided with separate sensor modules 390A and 390B in an alternative embodiment as illustrated at FIG. 3E. Note also that two adjacent flow lines may be protected by a single air detector or blood detector or both.

A key 409 of any desired shape may be placed on one of the lines 374 or 376 which fits into a slot 411 and engages a detector 410 to indicate its proper insertion into the slot 411. The key 409 and slot 411 ensure that if only one line 374 is protected by air sensor 401, that it is the venous line. Otherwise the protection system wherein flow is reversed to indicate a leak would serve no purpose. The detector 410 may send a signal along the signal line 378 to indicate proper insertion. A failure of proper insertion while attempting to operate the system may cause the system to generate an alarm. A door 406 may be closed over the lines 374 and/or 376 to lock them in place. Electronic equivalents of key 409 and sensor 410 may also be provided.

Figure 4A:
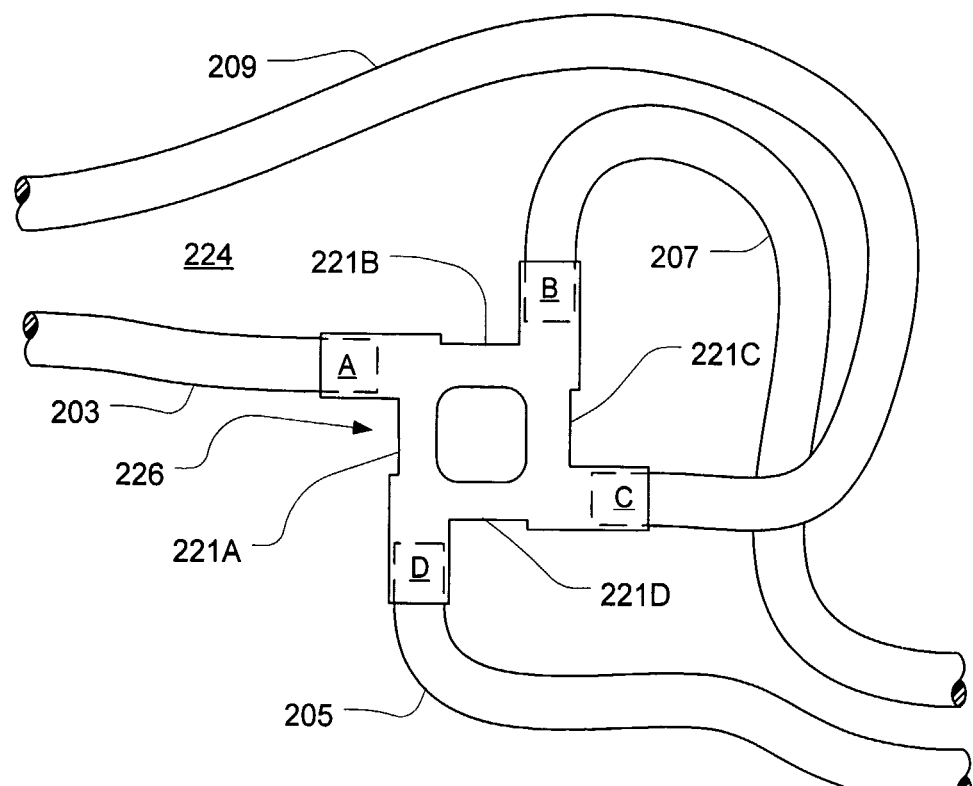
FIG. 4A illustrates a portion of a fluid circuit that is interoperable with an actuator to form a flow reversing device.
Figure 4B:
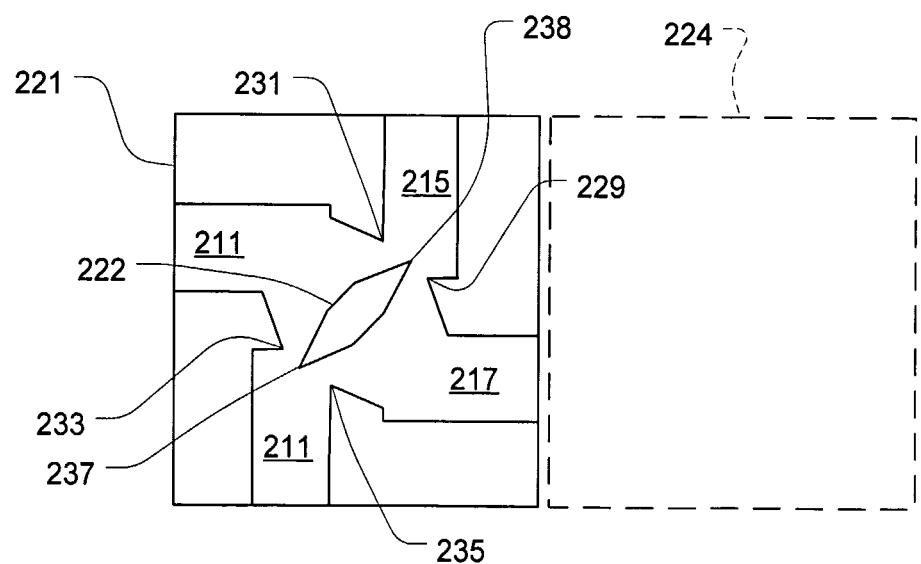
FIG. 4B illustrates an actuator interoperable with the fluid circuit portion illustrated in FIG. 4A.

Referring to FIGS. 4A and 4B, in an embodiment of a compact and reliable flow reversing device, a portion of a fluid circuit 224 includes a toroidal portion 226 with ports A, B, C, and D linked by segments 221A, 221B, 221C, and 221D as illustrated. Fluid lines 203, 205, 207, and 209 connect with respective ones of ports A, B, C, and D. The toroidal portion and portions of fluid lines 203, 205, 207, and 209 fit into channels 211, 215, 211, and 217 of an actuator 221. The actuator 221 contains a rotatable clamp 222 with two edges 238 and 237 which selectively pinch segments 221A, 221B, 221C, and 221D between the edges 238 and 237 and edges 231, 229, 235, and 233 of the actuator 221, respectively as illustrated in FIGS. 5A and 5B.

Figure 5A:
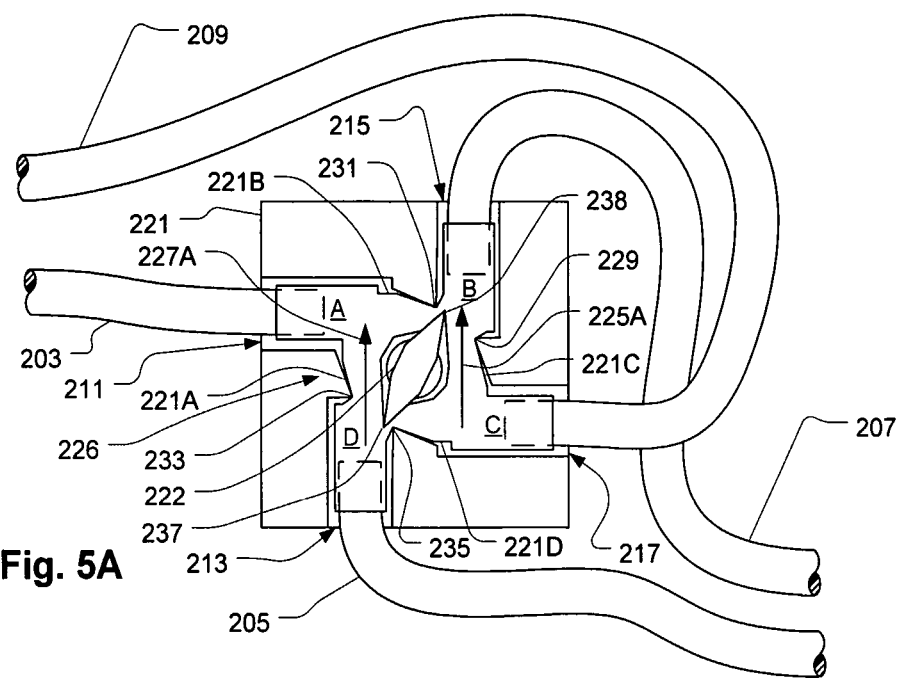
FIGS. 5A and 5B illustrate two operating modes of a flow reverser defined by the combination of the devices of FIGS. 4A and 4B.

Referring now to FIG. 5A, the toroidal portion 226 may be of a compliant and stretchable material that permits it to be forced into position in the actuator 221 and partly deformed as illustrated. The clamp 22 may be in the neutral position illustrated in FIG. 4B when this is done. During operation, when clamp 222 is in a first position indicated in FIG. 5A, segments 221B and 221D are clamped closed allowing a flow between line 209 to 207 and from line 205 to line 203 as indicated by arrows 225A and 227A. As will be observed, segment 221B is pinched between edges 238 and 231 while segment 221D is pinched between edges 237 and 235. The path of lines 209 to 207 may correspond to flow through the venous lines of the previous embodiments. For example, with reference to FIG. 3A, line 209 may correspond to line 325 and line 207 to line 337. Similarly, the path of lines 205 to 203 may correspond to flow through the arterial lines of the previous embodiments. For example, with reference to FIG. 3A, line 205 may correspond to line 335 and line 203 to line 329. In the configuration of FIG. 5A, the flow may then provide for normal blood flow for treatment by allowing 207 to flow blood to a patient and return through line 205 to pass through the flow reverser back to a blood treatment machine.

Figure 5B:
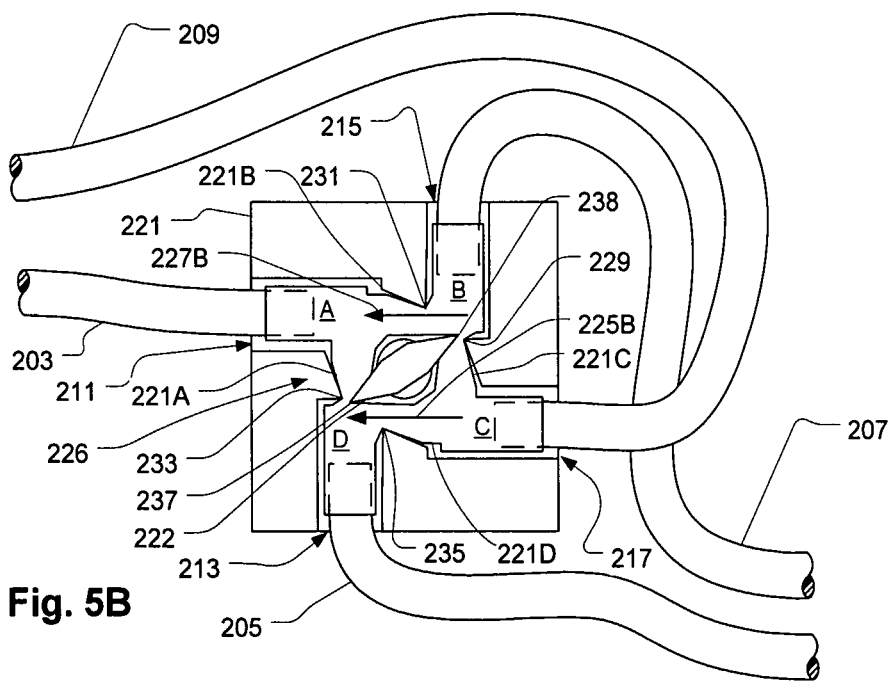

Referring now to FIG. 5B, when clamp 222 is in a first position indicated in FIG. 5B, segments 221A and 221C are clamped closed allowing a flow between line 209 to 205 and from line 207 to line 203 as indicated by arrows 225B and 227B. In the configuration of FIG. 5B, the flow may then provide for reverse blood flow for testing by allowing line 205 to flow blood to a patient and return through line 207 to pass through the flow reverser back to a blood treatment machine. This results in a negative pressure in line 207 whereupon if any disconnections or leaks occur, air will be drawn into line 207 which may be revealed by a sensor, as discussed with reference to the figures above.

Figure 6:
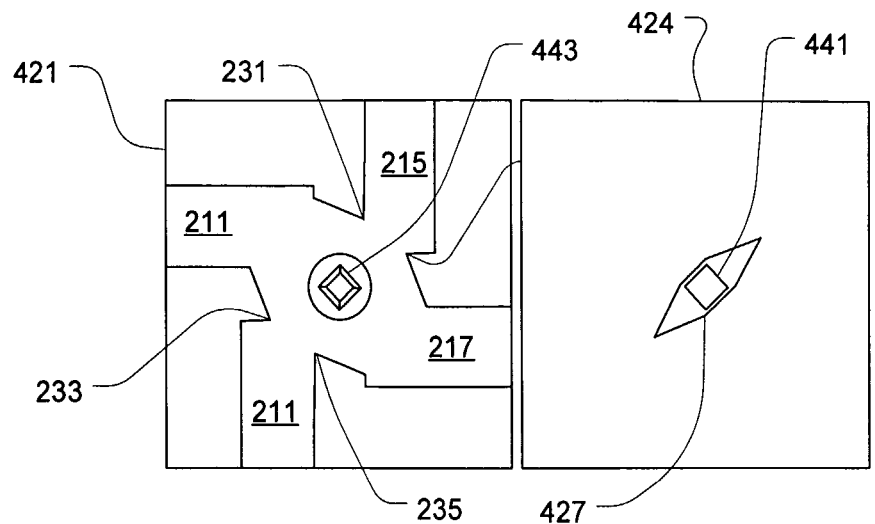
FIG. 6 illustrate a flow reversing actuator according to an alternative embodiment to that of FIGS. 4A, 4B, 5A, and 5B.
Figure 7:
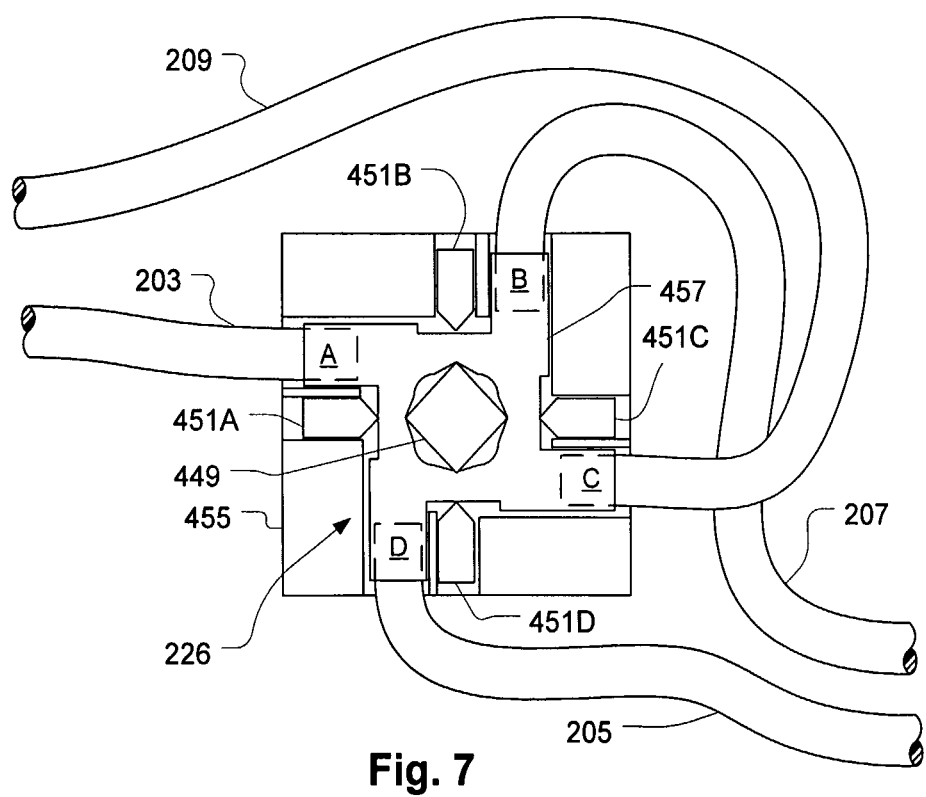
FIG. 7 illustrates a flow reversing device according to an alternative embodiment to that of FIGS. 4A, 4B, 5A, and 5B.

Referring now to FIGS. 6 and 7, in alternative embodiments of the flow reverser of FIGS. 5A and 5B a clamp 427 may be passively mounted on a door 424 and engaged with a drive bolt 443 in a chassis portion 421 of a flow reverser. The drive bolt 443 may fit as a key in a recess 441 thereby driving the clamp. The closure of the door 424 may be indicated by a detector which may send a signal to a controller permitting the drive bolt 443 to be operated according to the configuration of a controller (e.g., 349 of FIG. 3B). Instead of a single rotating clamp located at a center of a flow reverser, respective clamps 451A, 451B, 451C, and 451D may pinch respective portions of the flow circuit toroidal portion 226 by means of a shaped boss 449 that fits into the center of the toroidal portion 226. The claims 451A, 451B, 451C, and 451D may be operated by respective drives such as solenoids (not shown) or coupled to be operable with one or two drives as desired.

Figure 8A:
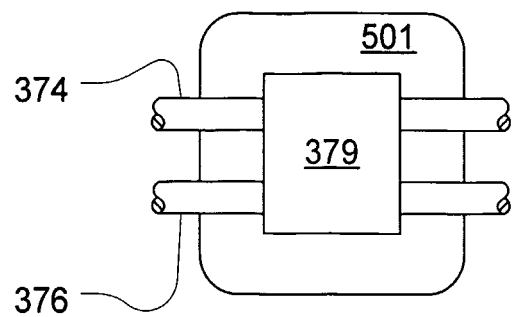
FIG. 8A illustrates a sensor module embedded in a soft outer casing.

Referring to FIG. 8A, to permit a flow reverser or sensor module to be placed close to the patient but allow for patient comfort, the flow reverser or sensor module 379 may be fitted into a soft shell 501. The latter may have a shape such as a teddy bear or other stuffed animal or ornament.

Figure 8B:
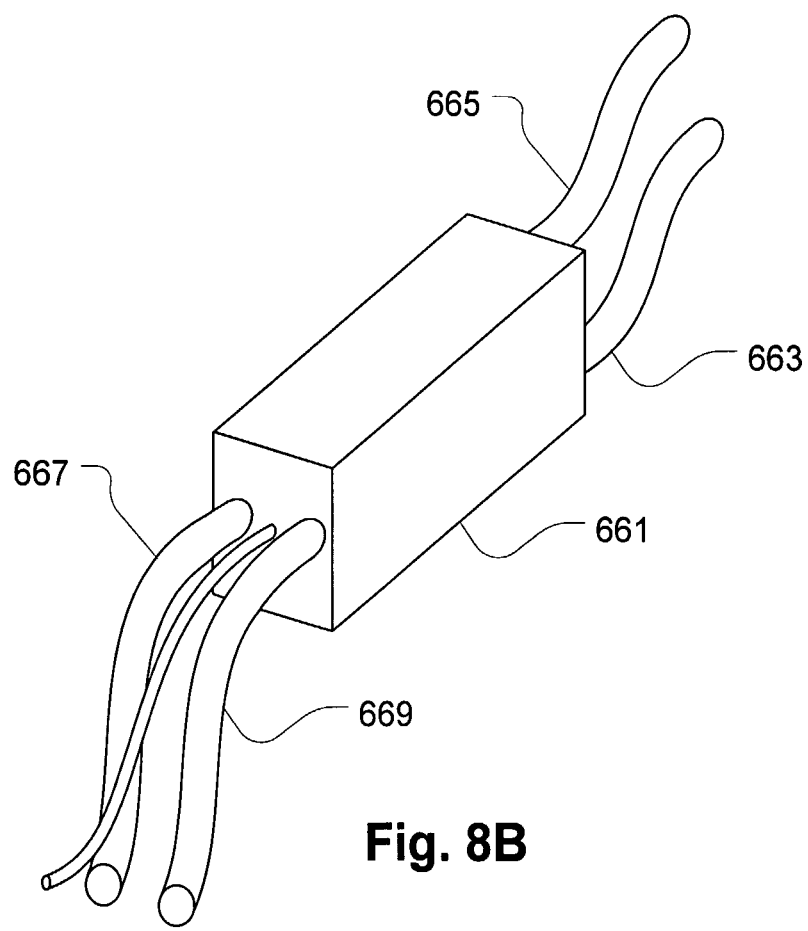
FIG. 8B illustrates a compact longitudinal reversing module.

Referring to FIG. 8B, preferably the flow reverser is of a compact longitudinal shape with the lines 667 and 669 leading to the blood treatment machine stemming from one end and the lines and the lines 663 and 665 leading to the patient access stemming from the opposite end. This may allow the flow reverser 661 to lie close to the patient access and self-orient in a comfortable and unobtrusive manner.

Figure 9B:
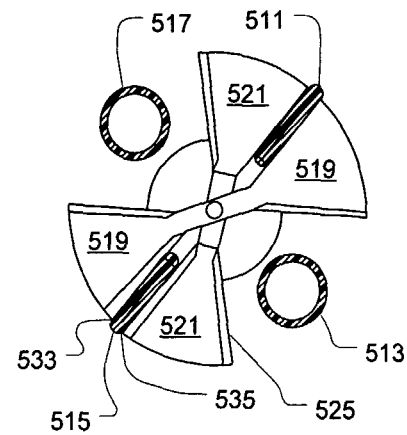
FIGS. 9A-9C illustrate a first embodiment of a fluid circuit portion and an actuator for providing a compact longitudinal flow reverser.
Figure 9A:
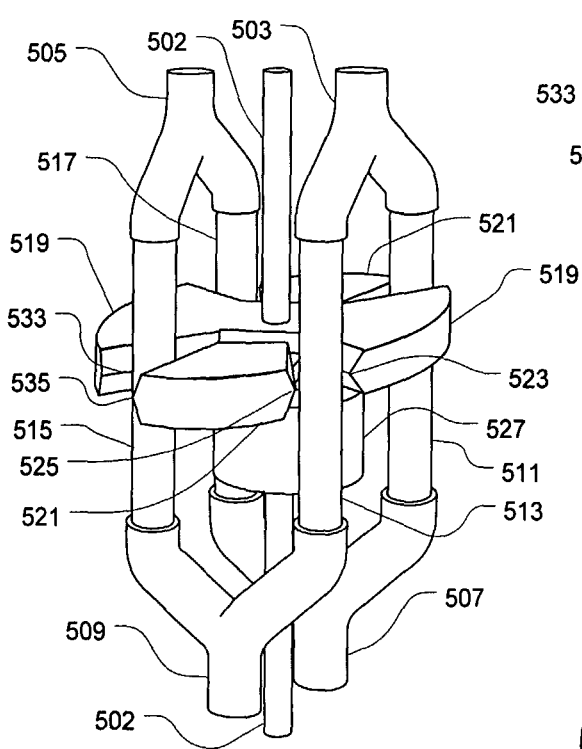
Figure 9C:
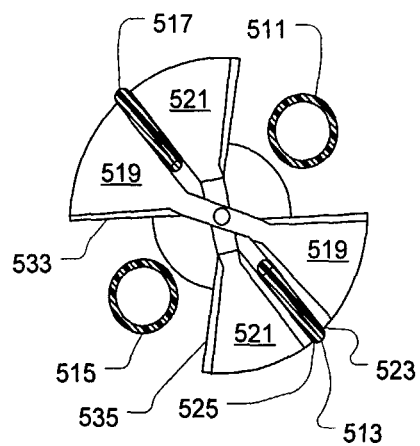

Referring to FIGS. 9A, 9B, and 9C, two Y-junctions 503 and 505 may be connected to a patient access and two other Y-junctions may be connected to a blood treatment machine or remainder thereof. Two double edged clamps 519 and 521 are driven by a double-axis motor drive 527 that rotates one clamp 519 in one direction and the other clamp 521 in the opposite direction, for example by providing that one clamp is connected to the stator and one connected to the rotor of the motor. It is contemplated that a reduction drive would be employed to increase the torque of the primary motor within the drive 527 and allow a small motor (not shown separately) to be used. A support stalk 502 holds the drive 527 so that it is free to rotate with respect to it, thereby providing a mounting to a housing such as illustrated in FIG. 8B. Each segment 511, 513, 515, and 517 may be selectively pinched by as illustrated in FIGS. 9B and 9C to provide for forward and reverse flow between one pair of junctions 505/503 or 509/507. The clamps may be tapered to provide a high clamping pressure as indicated at 535, 533, 523, and 525 and similarly on portions opposite the edges indicated at 535, 533, 523, and 525.

Note that the tubing structure of FIG. 9A which includes parallel segments 511, 513, 515, and 517, and the four Y-junctions 503 and 505, 507, and 509, is toroidal in shape, which can be confirmed by inspection. It will be observed that a planar projection (that is, a mapping or projection, as of a shadow, onto a plane, as of a shadow onto a surface) of the structure 511, 513, 515, and 517, 503, 505, and 507 with a plane perpendicular to parallel segments 511, 513, 515, and 517 and a projection direction parallel to parallel segments 511, 513, 515, and 517, is shaped as a ring.

Figure 10A:
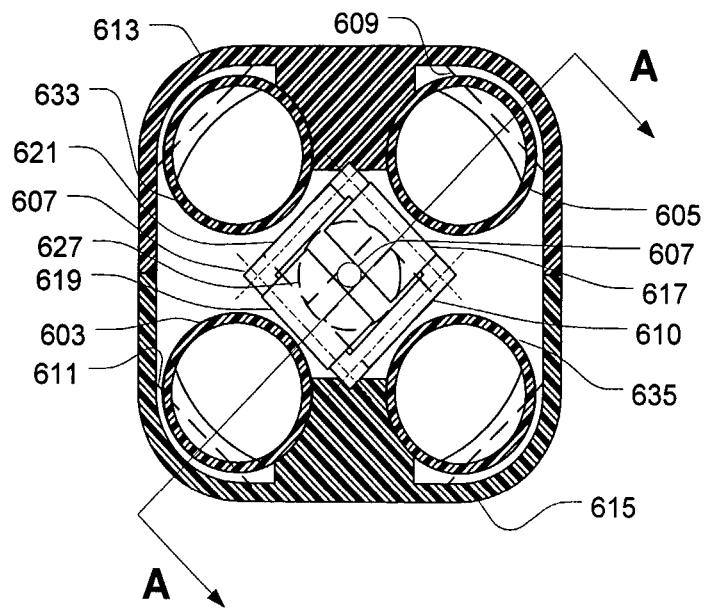
FIGS. 10A and 10B illustrate a second embodiment of an actuator for providing a compact longitudinal flow reverser.
Figure 10B:
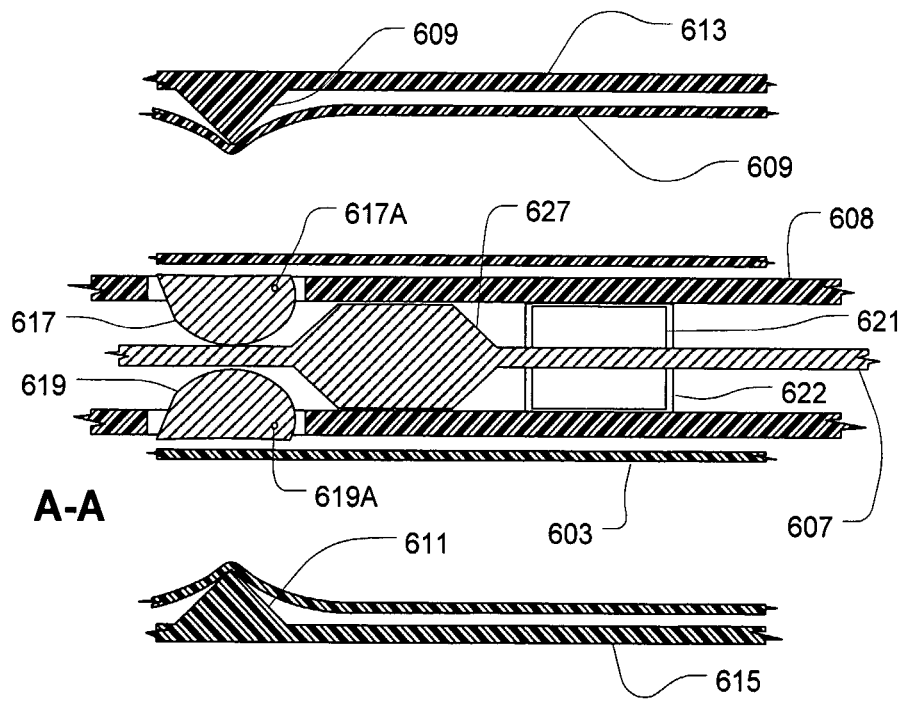

Referring to FIGS. 10A and 10B, another flow reversing device using a fluid circuit portion as illustrated in FIG. 9A producing four parallel segments 511, 513, 515, and 517 is driven by a linear drive (not shown) that moves a stalk 607 along an axis thereof. Cams 617 and 619 are forced into an opposing pair of tube segments 605 and 611 when a large diameter portion 627 of the stalk 607 is forced between the cams 617 and 619 by pushing the stalk 607 in a first direction (to the left). Cams 617 and 619 are forced into an opposing pair of tube segments 633 and 635 when a large diameter portion 627 of the stalk 607 is forced between the cams 610 and 621 by pushing the stalk 607 in a second opposite direction (to the right). The segments may be held in position by a frame of two portions 613 and 615 which close around a cam frame 607. Edges 609 and 611 are provided to amplify the pinching stress and cooperative with cams 617 and 619 to clamp the tubes segments 603 and 609.

Figure 11:
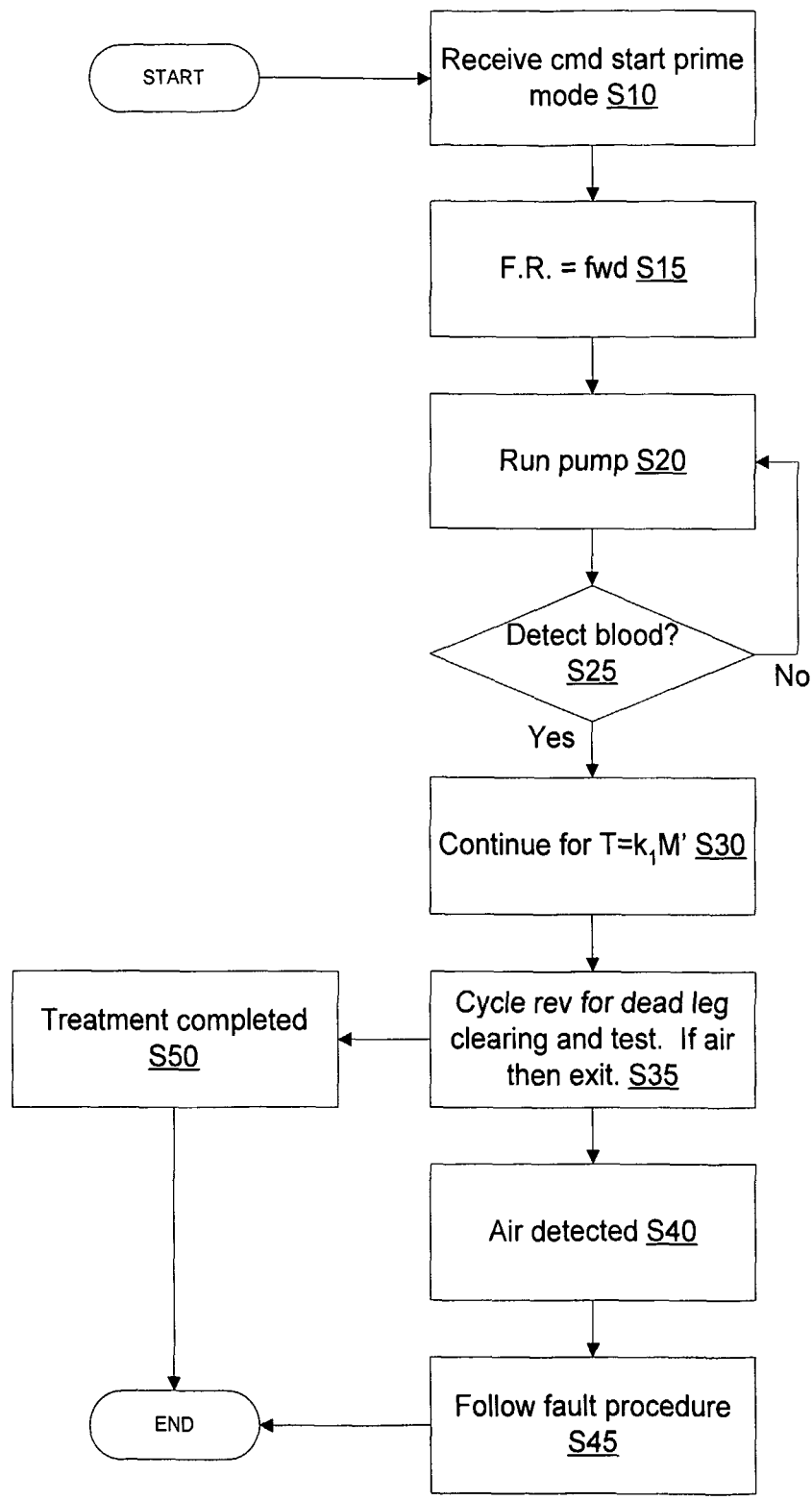
FIG. 11 is a flow chart for describing a control embodiment in which blood flow is reversed according to multiple schedules.

Referring to FIG. 11, an operating regimen begins with a priming of a fluid circuit at step S10. The priming mode is initiated by a priming command being received by the flow reverser controller at step S10. The flow reverser controller places the flow reverser in forward mode so that fluid is pumped in a single direction. The controller may be configured to operate for flow in a single direction continuously as long as no blood is detected by blood sensors in the sensor module or in the blood treatment machine. The pump may be operated at step S20 for a desired period of time to prime the blood circuit and other portions of the fluid circuit used for treatment. At some point during the priming mode, the operator may halt the pump, clamp various lines, and make certain connections in preparation for treatment and restart the pump. All these steps are assumed to fall within step S20.

Figure 12:
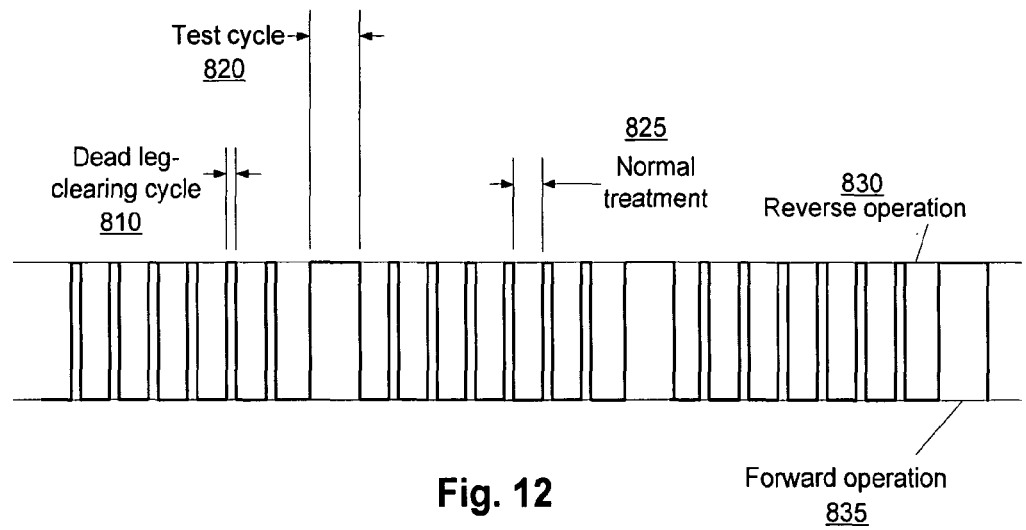
FIG. 12 is a time plot of blood flow for use in describing the control regime of FIG. 11.
Figure 13:
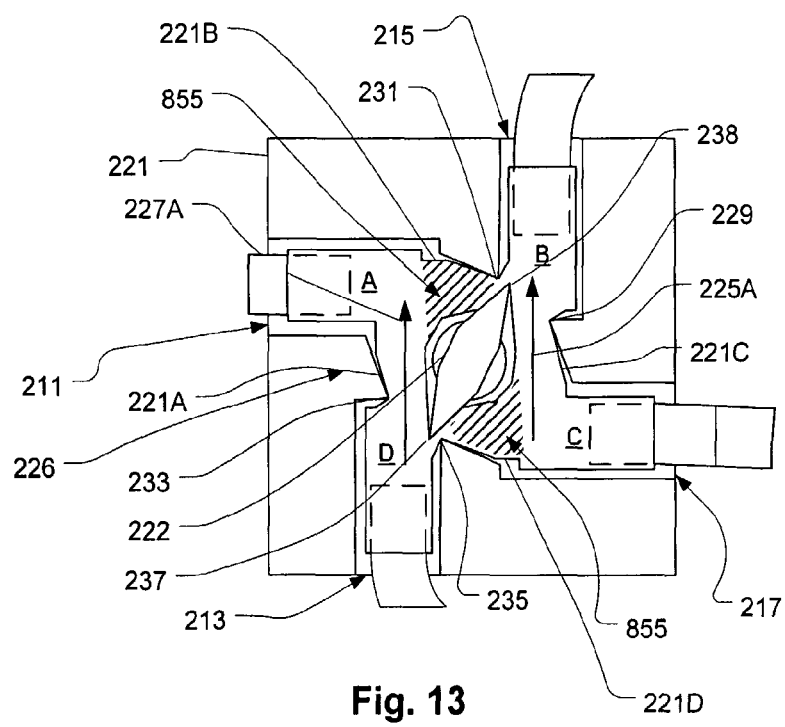
FIG. 13 is an illustration of stagnant flow regions for illustrating the flow control regime of FIGS. 11 and 12.

When the flow reverser controller detects blood in step S25, control flow exits to step S30 and flow continues in the same direction for a specified period of time which may be proportional to the mass flow rate of blood. The blood will ordinarily be detected because of the connection changes of the operator who has determined that the system is adequately primed and has remade connections as required. This may also be an automated process as well depending on the blood processing system and the level of automation. Referring now also to FIG. 12, once the initial forward operation period has elapsed at step S30, the flow reverser control may go into an operating mode where it periodically reverses flow 830 for a fixed interval test cycle 820 to generate a temporary negative pressure and reverse flow to test the venous line and then returns to forward operation 835. Generally, the test cycle 820 interval will be shorter than the normal forward treatment 825 interval. In addition to the test cycle, short duration reverse cycles 810 are a higher frequency may be included to clear the dead legs of the flow reversing device. Referring momentarily to FIG. 13, the shaded regions 815 in the embodiment of FIGS. 5A and 5B in the normal flow direction represent areas with no flow. If the blood in these regions is allowed to stagnate for an extended time, clotting may occur. To help prevent this, the flow may be reversed for very short intervals to cause a flow in these otherwise continuously non-flow regions 855. A train of such dead-leg clearing cycles is shown in FIG. 12 at 810.

Returning to FIG. 11, the cyclical operation of FIG. 12 may continue until a treatment is completed or until air is detected (or some other malfunction causes treatment to be terminated). For retrofit embodiments of the flow reversing leak detection system such as illustrated in FIGS. 3A and 3C for example, it is desirable for the flow reversing controller to respond to air detection in a manner that ensures an appropriate response without some sort of control connection or control collaboration between the flow reversing module (e.g. 370, FIG. 3C) and the blood treatment machine 320. Thus, preferably the flow reversing module control's 349 response should ensure appropriate action. Referring now to FIG. 14A, to that end a response S45A for step S45, when air is detected at step S40, the blood lines may be clamped at step S60 to induce a high pressure in the blood treatment machine which in most type of blood treatment machines would trigger a shutdown and error indication by the machine. This may be provided by means of a clamp as indicated at 326 or 317 in FIGS. 3B and 2B respectively, for example. Referring to FIG. 14B, another response for step S45 is step S45A in which a shutdown by the main processing machine is induced in step S65 to continue operating in reverse mode until the air that was detected by the flow reversing module triggers an air detection by the blood processing machine.

Note that by placing the air sensor close to a patient as described in the foregoing embodiments, the reverse cycle may be kept to a minimum duration. Preferably this duration is established to provide the minimum volume displacement needed to cause any air bubbles leaking into the blood line to reach the air sensor in the sensor module. This may be established in the flow reverser by means of an input from a user or by calculating from a measured flow rate. Thus, a flow rate sensor may be included in the flow reversing module and the controller configured to calculate the amount of time, based on flow rate, to ensure the minimum volume is displaced.

The invention claimed is:

1. A flow reversing device for performing blood treatment, comprising:
a flow reversing actuator that receives and engages a disposable tubing set with multiple tubing branches which form forward and reverse blood flow paths respectively when blood the flow reversing actuator is selectively changed between forward and reverse configurations, the shape of the tubing being such that during forward operation, dead regions of non-flowing blood are defined;
said dead regions including portions of said tubing branches of a predefined volume; and
a controller, operatively connected to the flow reversing actuator, the controller configured to operate in a forward mode and at first times, for first intervals sufficient at a first frequency to cause said reversing actuator to clear the dead regions by displacing blood of said predefined volume, and at second times for second intervals at a second frequency to test for leaks by reversing the flow of blood for a period of time sufficient to cause air to be drawn into the tubing set and conveyed to an air sensor, thereby to indicate a leak;
where the first intervals are shorter than the second, the first frequency is greater than the second frequency.

2. The device of claim 1, wherein the controller is configured to cause said reversing actuator to clear the dead regions more frequently than it tests for leaks.

3. The device of claim 2, wherein the duration of flow reversals occurring at said first times is shorter than flow reversals at said second times.

4. The device of any one of claims 1 to 3, wherein the reversing actuator comprises the air sensor.

5. The device of claim 4, wherein the flow reversing actuator is configured to block the blood flow paths; and
wherein the controller is configured to control the flow reversing actuator to block the blood flow paths in response to a detection of air by the air detector.

6. The device of claim 1, wherein the flow reversing actuator comprises:
a flexible ring-shaped structure defining a central opening surrounded by a non-wetted surface thereof, said ring-shaped structure having a wetted surface there within in fluid communication with multiple flow ports;
an actuator having a pivoting element with two ends, that fits within said ring-shaped structure, said actuator having fixed elements that with edges that oppose said two ends on respective sides such that when said pivoting element is pivoted in a first direction, it pinches a first two portions of said ring-shaped structure against a first two of said edges, said first two portions corresponding to a first two flow passages of said ring-shaped structure and such that when said pivoting element is pivoted a second direction, it pinches a second two portions of said ring-shaped structure against a second two of said edges, said second two portions corresponding to a second two flow passages of said ring-shaped structure, a configuration of said ports being such that communication between a first two of said flow ports is blocked while fluid communication between a second two of said flow ports is permitted when said pivoting element is pivoted in said first direction while communication between a second two of said flow ports is blocked while fluid communication between a first two of said flow ports is permitted when said pivoting element is pivoted in said second direction.

7. The device of claim 6, wherein the fixed and pivoting elements are arranged to define a ring-shaped recess into which said ring-shaped structure fits.

8. The device of claim 1, wherein the flow reversing actuator comprises:
a flexible valve body linking together, for fluid communication, fluid ports fluidly connected by said valve body;
a first portion of an actuator with at least one first pinching element;
a second portion of said actuator that moves relative to said first portion;
said valve body forming a structure that surrounds the first portion, said valve body being at least partly confined within the second portion, said second portion having at least one second pinching element opposing said at least one first pinching element;
in a first configuration, said actuator pinching said valve body such that a first pair of said fluid ports are linked for fluid communication while a second pair is blocked;
in a second configuration, said actuator pinching said valve body such that said second pair of said fluid ports are linked for fluid communication while said first pair is blocked.

9. The device of claim 8, wherein a planar projection of said valve body is ring-shaped.

10. The device of claim 1, wherein the flow reversing actuator comprises:
a pair of patient-side ports for connection to a patient access;
a pair of treatment-side ports for connection to a blood processing machine;
a reversing valve configured to allow blood to flow between said patient-side and said treatment-side ports in two selected directions of flow, such that blood flow from said patient-side ports and said patient access is selectively reversible;

wherein the reversing valve has a flexible valve body that forms a structure surrounding a first portion of an actuator with at least one first pinching element;

a second portion of said actuator is constructed to move relative to said first portion and has at least one second pinching element opposing said at least one first pinching element;

in a first configuration, said actuator pinches said valve body such that a first pair of said ports is linked for fluid communication while a second pair is blocked; and in a second configuration, said actuator pinches said valve body such that the second pair of said ports is linked for fluid communication while the first pair is blocked.

11. The device of claim 10, further comprising a housing having said patient side ports on a first end and said treatment-side ports on a second end, whereby said flow reversing device may be located close to said patient access and remote from a blood treatment machine.

12. The device of claim 10, wherein said reversing valve is configured to block blood flow through said treatment-side ports and said controller is configured to control said reversing valve to block said blood flow in response to a detection of air in blood by said air detector.

13. The device of claim 1, wherein the controller is configured to run at a flow rate and a duration spanning said first times such that a lower volume of blood is pumped during said first times than during said second times.

14. The device of claim 1, wherein the first times are shorter than the second times.

15. The device of claim 13, wherein the flow rate and the duration of said first times are not sufficient to cause air to be drawn into the tubing set and conveyed to an air sensor, but sufficient to clear said dead regions.

* * * * *